United States Patent [19]

Benjamin et al.

[11] Patent Number: 4,898,980

[45] Date of Patent: Feb. 6, 1990

[54] PROCESS FOR PREPARING DITHIOBISPHENOLS

[75] Inventors: Linda A. Benjamin, Horsham, Pa.; Stephen D. Pastor, Basel, Switzerland; John J. Luzzi, Carmel, N.Y.

[73] Assignee: Ciba-Geigy Corporation, Ardsley, N.Y.

[21] Appl. No.: 212,852

[22] Filed: Jun. 29, 1988

[51] Int. Cl.$^4$ ............................................. C07C 148/02
[52] U.S. Cl. ......................................................... 568/23
[58] Field of Search ........................................... 568/23

[56] References Cited

U.S. PATENT DOCUMENTS

| | | | |
|---|---|---|---|
| 3,377,333 | 4/1968 | Clesiolski et al. | 260/97.6 |
| 3,377,334 | 4/1968 | McBride et al. | 260/98 |
| 3,423,389 | 1/1969 | Wheekes | 260/97.5 |
| 3,468,961 | 9/1969 | Gouring | 568/64 |
| 3,479,407 | 11/1969 | Laufer | 568/23 |
| 3,649,595 | 3/1972 | Kline | 524/332 |
| 3,812,192 | 5/1974 | Gables et al. | 568/23 |
| 3,919,171 | 11/1975 | Martin | 568/48 |
| 3,957,064 | 4/1976 | Whalley | 568/64 |

FOREIGN PATENT DOCUMENTS 0200212  11/1986  .

OTHER PUBLICATIONS

Onoue et al., Chem. Abstracts, vol. 106:66895j (1987).

*Primary Examiner*—Mary E. Ceperley
*Attorney, Agent, or Firm*—Harry Falber

[57] ABSTRACT

An improved process for preparing dithiobisphenols wherein the appropriate phenol is reacted with sulfur monochloride in the presence of substantially molar amounts of an aliphatic or heterocyclic amine.

6 Claims, No Drawings

PROCESS FOR PREPARING DITHIOBISPHENOLS

PROCESS FOR PREPARING DITHIOBISPHENOLS

Dithiobisphenols are known for a variety of uses. For example, U.S. Pat. No. 3,377,333, U.S. Pat. No. 3,377,334 and U.S. Pat. No. 3,423,389, among others, disclose the use of such materials as catalysts and bleaching agents in rosin acid esterification.

It is also known that the dithiobisphenols can be synthesized in a variety of manners. A dominant procedure is the reaction of phenols with sulfur monochloride in a variety of solvents. The above noted patents as well as U.S. Pat. No. 3,479,407, U.S. Pat. No. 3,649,595, and the like, describe such a process. However, such an approach generally results in over-sulfidation and a concomitant formation of undesirable polysulfides, thereby significantly lowering the yield of disulfide. Subsequent purification of these mixtures is difficult such that significant yield increase is not achieved.

Other approaches involving oxidation and reduction reactions are also known. However, the starting materials in these reactions are generally more expensive or require a multi-step synthesis. In addition, mono- and polysulfides have been prepared by the reaction of a phenol with either sulfur chloride (U.S. Pat. No. 3,812,912, U.S. Pat. No. 3,919,171, U.S. Pat. No. 3,952,064) or elemental sulfur (U.S. Pat. No. 3,468,961).

Particular reference is made to Europe 200,212 which prepares polythiobisphenols by reacting phenol and sulfur monochloride in the presence of catalytic amounts (1-30%, by weight of phenol) of tertiary amines, quaternary ammonium salts, alkylated acid amides and heteroaromatic compounds and in a polar organic solvent. British 1,345,311 involves similar reactions absent catalysts but utilizes N,N-dimethylformamide or N-methylpyrrolidone as the solvent. In each instance, the achieved yield of desired disulfide product is reduced by the general polysulfide formation.

Accordingly, it is the primary object of this invention to provide a process for synthesizing dithiobisphenols in high yields and in the substantial absense of mono- and trithiophenols.

It has now been discovered that by reacting phenols and sulfur monochloride in the presence of substantially molar amounts of amine, dithiobisphenols can be readily prepared. Advantages stemming from this approach include:

1. The process of the invention allows for the preparation of dithiobisphenols in high yield.
2. The process of the invention is industrially advantageous in that it allows for the preparation of dithiobisphenols in one step through the use of inexpensive starting materials.
3. The process of the invention utilizes moderate temperatures avoiding the problems and cost associated with higher temperature processes.
4. The process of the invention allows for the recovery and reuse of the starting amine.
5. The process of the invention allows for selective preparation of dithiobisphenols without the over sulfidation which results in polynuclear by-products or polysulfides.
6. The process avoids the use of the troublesome, and frequently toxic, dipolar aprotic solvents often utilized in prior processes.
7. The process is particularly applicable for the preparation of 2,2'-dithiobis(4,6-di-tert.butylphenol) which is a preferred element in rosin acid esterification procedures.

The process of the invention involves reacting a phenol of the formula

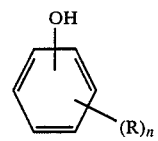

wherein R is $C_1$–$C_{18}$ alkyl, $C_5$–$C_{12}$ cycloalkyl, $C_7$–$C_9$ aralkyl or $C_7$–$C_9$ aralkyl substituted by $C_1$–$C_{12}$ alkyl; and n is 1–3; with sulfur monochloride in the presence of substantially molar amounts of an aliphatic or heterocyclic amine, to prepare dithiobisphenols of the formula

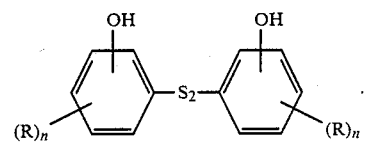

Preferred phenols exhibit R as $C_1$–$C_8$ alkyl, $C_5$–$C_6$ cycloalkyl, benzyl and alpha-methylbenzyl, and n as 2. Typical phenols include 2,4-di-tert.butyl-phenol, 2,6-di-tert.butylphenol, 2-methyl-6-tert.butylphenol, 2,4-di-tert.octylphenol, 2,4-dimethylphenol, and the like.

Applicable amines include aliphatic amines, preferably tertiary aliphatic amines such as triethylamine, tributylamine, trimethylamine, triethylenediamine and tetraethylene diamine, and heterocyclic amines such as pyridine, 2-chloropyridine, alpha-picoline and β-picoline. The amine is present in molar amounts ±10% relative to the phenol, and preferably in equimolar amounts.

The reaction may be conducted in a solvent, preferably a hydrocarbon solvent such as toluene, xylene, benzene, hexane and heptane. The reaction will be conducted at temperatures ranging from −30° C. to the boiling point of the solvent and preferably from −5° to +5° C. Subsequent isolation of the dithiobisphenol provides high yields of desired product and the substantial absence of other than the dithio product.

The following examples further illustrate the embodiments of the invention.

EXAMPLE 1

A solution of 25.0 g (120 mmol) of 2,4-di-tert-butylphenol and 12.2 g (120 mmol) of triethylamine in 150 ml of toluene at −5° to 0° C. is admixed dropwise with 4.84 ml (60 mmol) of sulfur monochloride in 50 ml of toluene over a 0.5 hour period. When the addition is complete, the reaction mixture is stirred for an additional hour at −5° to 0° C. The reaction mixture is then stirred overnight at room temperature. The reaction mixture is filtered to remove 16.23 g (98%) of triethylamine hydrochloride. The filtrate is extracted sequentially with water and brine and the organic phase is dried over anhydrous sodium sulfate. The solvent is removed in vacuo and the residue is recrystallized from acetonitrile to give 19.9 g (69.3%) of a pale yellow solid: mp 111°–113° C.

An evaluation of the product revealed no monothio content and only 0.04 parts of trithio compound for every part of dithio compound.

The procedure is then repeated except that a molar amount of pyridine is introduced as a replacement for the triethylamine. The resulting product is dominantly the dithio component, there being no monothio component and only 0.12 parts of trithio component per part of dithio product.

EXAMPLE 2

This example illustrates the beneficial use of molar quantities of triethylamine.

The procedure of Example 1 is repeated using 25.0 grams (120 mmol) of 2,4-di-tert-butylphenol, 4.84 ml (60 mmol) of sulfur monochloride and a catalytic amount (30 wt%) of triethylamine in toluene at −5° to 0° C. to give a mixture of the corresponding mono-, di- and trisulfides.

| Et$_3$N | —S— | —SS— | —SSS— |
|---|---|---|---|
| 30 wt % | 0.44 | 1.0 | 0.32 |
| Molar | — | 1.0 | 0.04 |

It is seen that the use of catalytic amounts of amine results in a much greater diversity of product, the preferred dithio product being present with significant amounts of both the mono- and trithio components. In contrast, the use of substantially molar amounts pursuant to this invention virtually eliminates the occurrence of these undesirable products.

What is claimed is:

1. A process of preparing compounds of the formula

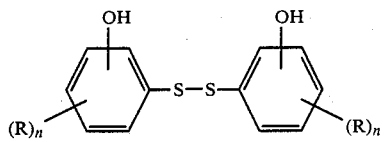

wherein R is $C_1$–$C_8$ alkyl, $C_5$–$C_{12}$ cycloalkyl, $C_7$–$C_9$ aralkyl or $C_7$–$C_9$ aralkyl substituted by $C_1$–$C_{12}$ alkyl and n is 1–3, which comprises reacting a phenol of the formula

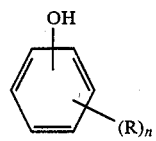

wherein R and n are as previously defined with sulfur monochloride in the presence of equimolar amounts ±10% and greater than 30 weight %, relative to the phenol, of an aliphatic or heterocyclic amine.

2. The process of claim 1, wherein R is $C_1$–$C_8$ alkyl, $C_5$–$C_6$ cycloalkyl, benzyl and alpha-methylbenzyl and n is 2.

3. The process of claim 1, wherein said phenol is 2,4-di-tert.butylphenol, 2,6-di-tert.butylphenol, 2-methyl-6-tert.butylphenol, 2,4-di-tert.octylphenol or 2,4-dimethylphenol.

4. The process of claim 1, wherein said amine is a tertiary aliphatic amine.

5. The process of claim 4, wherein said amine is triethylamine, trimethylamine, tributylamine, triethylenediamine or tetraethylenediamine.

6. The process of claim 1, wherein said heterocyclic amine is pyridine, 2-chloropyridine, alpha-picoline or β-picoline.

* * * * *